US008329654B2

(12) United States Patent
Deglon et al.

(10) Patent No.: US 8,329,654 B2
(45) Date of Patent: Dec. 11, 2012

(54) USE OF IL-6/IL-6 CHIMERA IN HUNTINGTON'S DISEASE

(75) Inventors: Nicole Deglon, Curtilles (CH); Patrick Aebischer, Villette (CH); Jean-Charles Bensadoun, Chenes-Bougeries (CH)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 12/717,305

(22) Filed: Mar. 4, 2010

(65) Prior Publication Data

US 2010/0166703 A1   Jul. 1, 2010

Related U.S. Application Data

(63) Continuation of application No. 11/622,284, filed on Jan. 11, 2007, now abandoned, which is a continuation of application No. 10/380,427, filed as application No. PCT/EP01/10442 on Sep. 10, 2001, now abandoned.

(30) Foreign Application Priority Data

Sep. 14, 2000 (EP) .................................... 00120045

(51) Int. Cl.
*A61K 38/00* (2006.01)
*A61K 38/16* (2006.01)
(52) U.S. Cl. ..................................... 514/17.7; 514/21.2
(58) Field of Classification Search .......................... None
See application file for complete search history.

(56) References Cited

U.S. PATENT DOCUMENTS

| 5,462,731 | A | 10/1995 | Aderka et al. |
| 5,637,483 | A | 6/1997 | Dranoff et al. |
| 5,792,900 | A | 8/1998 | Lee et al. |
| 6,312,683 | B1 | 11/2001 | Kingsman et al. |

FOREIGN PATENT DOCUMENTS

| WO | WO 99/02552 | 1/1999 |
| WO | WO 00/78331 | 12/2000 |

OTHER PUBLICATIONS

Levine 1999 Journal of Neuroscience Research 58:515-532.*
Carlson 1999 Journal of Immunology 163:3963-3968.*
Ikeda 1996 Brain Research 726:91-97.*
Ramaswamy et al., Animal Models of Huntington's Disease, 2007, ILAR Journal 48(4):356-373.*
Bosco et al., BDNF and NT-4 Differentially Modulate Neurite Outgrowth in Developing Retinal Ganglion Cells, Sep. 15, 1999, Journal of Neuroscience Research 57(6):759-769.*
Schäfer et al., "The IL-6/sIL-6R Fusion Protein Hyper-IL-6 Promotes Neurite Outgrowth and Neuron Survival in Cultured Enteric Neurons", *Journal of Interferon and Cytokine Research*, 19:527-532 (1999).
März et al., "Sympathetic Neurons Can Produce and Respond to Interleukin 6", *Proc. Natl. Acad. Sci. USA*, 95:3251-3256 (1998).
Murakami-Mori et al., "The Soluble Form of the IL-6 Receptor (sIL-6Rα) is a Potent Growth Factor for AIDS-Associated Kaposi's Sarcoma (KS) Cells; The Soluble Form of gp130 is Antagonistic for sIL-6Rα-Induced AIDS-KS Cell Growth", *International Immunology*, 8(4):595-602 (1996).
Hoischen et al., "Human Herpes Virus 8 Interleukin-6 Homologue Triggers gp130 on Neuronal and Hematopoietic Cells", *Eur. J. Biochem.*, 267:3604-3612 (2000).
Database WPI: Abstract for JP 2000 248000, "Differentiation Promoter for nervous System Cell of Nerve Progenitor Cell, Contains Fusion Proteins of Interleukin-6 Receptor and Interleukin-6 as Active Ingredient", Tosoh Corp, Sep. 12, 2000.
Andersen, KD et al., "Ciliary neurotrophic factor protects striatal output neurons in an animal model of Huntington disease"; Proc. Natl. Acad. Sci., Jul. 1996; pp. 7346-7351, vol. 93; USA.
Altschul, Stephan F. et al., "Basic Local Alignment Search Tool", J. Mol. Biol., 1990; pp. 403-410, vol. 215; Academic Press Limited.
Altschul, Stephan F. et al., "Gapped BLAST and PSI-BLAST: a new generation of protein database search programs", Nucleic Acids Research, 1997; pp. 3389-3402, vol. 25; Oxford University Press.
Beal, M. Flint, "Chronic Quinolinic Acid Lesions in Rats Closely Resemble Huntington's Disease", The Journal of Neuroscience, Jun. 1991; pp. 1649-1659, vol. 11(6); Society of Neuroscience.
Bemelmans, A-P et al., "Brain-Derived Neurotrophic Factor-Mediated Protection of Striatal Neurons in an Excitotoxic Rat Model of Huntington's Disease, as Demonstrated by Adenoviral Gene Transfer'", Human Gene Therapy, Dec. 10, 1999; pp. 2987-2997, vol. 10; Mary Ann Liebert, Inc.
Bensadoun, J-C et al., "Lentiviral Vectors as a Gene Delivery System in the Mouse Midbrain: Cellular and Behavioral Improvements in a 6-OHDA Model of Parkinson's Disease Using GDNF", Experimental Neurology, 2000; pp. 15-24, vol. 164; Academic Press.
Borlongan, C.V. et al., "Asymmetrical motor behavior in rats with unilateral striatal excitotoxic lesions as revealed by the elevated body swing test", Brain Research, 1995; pp. 231-234, vol. 676; Elsevier Science B.V.
Beighton, P. and Hayden, M.R., "Correspondence", SA Medical Journal, Feb. 21, 1981; pp. 250-252.
Chebath, Judith et al., "Interleukin-6 receptor-interleukin-6 fusion proteins with enhanced interleukin-6 type pleiotrophic activities", Eur. Cytokine Nets., Dec. 1997; pp. 359-365, vol. 8 No. 4.
Choi, Dennis W., "Glutamate Neurotoxicity and Diseases of the Nervous System", Neuron, Oct. 1988; pp. 623-634, vol. 1; Cell Press.
Devereux, John et al., "A comprehensive set of sequence analysis programs for the VAX", Laboratory of Genetics, Aug. 18, 1983; pp. 387-395, vol. 12, No. 1; University of Wisconsin, Madison WI.
Ellison, DW et al., "Subset of Neurons Characterized by the Presence of NADPH-Diaphorase in Human Substantia Innominata", The Journal of Comparative Neurology, 1987; pp. 233-245, vol. 260; Alan R. Liss, Inc.
Emerich, DF et al., "Cellular Delivery of Human CNTF Prevents Motor and Cognitiv Dysfunction in a rodent model of Huntington's Disease", Cell Transplantation, 1997; pp. 249-266, vol. 6, No. 3;Elsevier Science Inc., USA.
Emerich, DF et al., "Implants of Encapsulated Human CNTF-Producing Fibroblasts Prevent Behavioral Deficits and Striatal Degeneration in a Rodent Model of Huntington's Disease", The Journal of Neuroscience, Aug. 15, 1996; pp. 5168-5181, vol. 16 (16); CytoTherapeutics, Inc., Providence, Rhode Island.

(Continued)

*Primary Examiner* — John Ulm
(74) *Attorney, Agent, or Firm* — Browdy and Neimark, PLLC

(57) ABSTRACT

The invention relates to the use of an IL-6R/IL-6 chimera, a mutein, isoform, fused protein, functional derivative, active fraction or circularly permutated derivative or a salt thereof, for the manufacture of a medicament for the treatment and/or prevention of Huntington's disease.

4 Claims, 5 Drawing Sheets

OTHER PUBLICATIONS

Emerich, DF et al., "Protective effect of encapsulated cells producing neurotrophic factor CNTF in a monkey model of Huntington's disease", Nature, Mar. 27, 1997; pp. 395-399, vol. 386; Alkermes, Inc., Cambridge, Massachusetts.

Emerich, DF et al., "Implantation of Polymer-Encapsulated Human Nerve Growth Factor-Secreting Fibroblasts Attenuates the Behavioral and Neuropathological Consequences of Quinolinic Acid Injections into Rodent Striatum", Experimental Neurology, 1994; pp. 141-150, vol. 130; Academic Press, Inc.

Fischer, Martina et al., "A bioactive designer cytokine for human hematopoietic progenitor cell expansion", Nature Biotechnology, Feb. 1997; pp. 142-145, vol. 15.

Gadient, Reto A., "Interleukin-6 (IL-6) A molecule with both beneficial and destructive potentials", Progress in Neurobiology, 1997; pp. 379-390, vol. 52; Elsevier Science Ltd., Great Britain.

Greenamyre, JT et al., "Alterations in L-Glutamate Binding in Alzheimer's and Huntington's Diseases", Science; pp. 1496-1499, vol. 227.

Haggiag, S. et al., "Induction of myelin gene expression in Schwann cell cultures by an interleukin-6 receptor-interleukin-6 chimera", FEBS Letters, 1999; pp. 200-204, vol. 457; Federation of European Biochemical Societies.

Halimi, Hubert et al., "Epitope peptides from interleukin-6 receptor which inhibit the growth of human myeloma cells", Eur. Cytokine Netw., May-Jun. 1995; pp. 135-143, vol. 6, No. 3.

Hirano, Toshio et al., "Signal Transduction through gp130 that is Shared among the Receptors for the Interleukin 6 Related Cytokine Subfamily", Stem Cells, 1994; pp. 262-277, vol. 12.

Hirota, H. et al., "Accelerated Nerve Regeneration in Mice by Upregulated Expression of Interleukin (IL) 6 and IL-6 Receptor after Trauma", J. Exp. Med, Jun. 1996; pp. 2627-2634, vol. 183; The Rockefeller University Press.

Hottinger, A.F. et al., "Complete and Long-Term Rescue of Lesioned Adult Motoneurons by Lentiviral-Mediated Expression of Glial Cell Line-Derived Neurotrophic Factor in the Facial Nucleus", The Journal of Neuroscience, 2000; pp. 5587-5593, vol. 20 (15).

Katz, Anne, "Increased sensitivity of IL-6-deficient mice to carbon tetrachloride hepatotoxicity and protection with an IL-6 receptor-IL-6 chimera," Cytokines, Cellular & Molecular Therapy!, 1998; pp. 221-227, vol. 4; Martin Dunitz Ltd.

Klimatcheva, Ekaterina et al., "Lentiviral Vectors and Gene Therapy", Frontiers in Bioscience, Jun. 1, 1999; pp. 481-496, vol. 4.

Kordower, Jeffrey H., "Lentiviral Gene Transfer to the Nonhuman Primate Brain", Experimental Neurology, 1999; pp. 1-16, vol. 160; Academic Press.

Kordower, Jeffrey H. et al., "Grafts of EGF-Responsive Neural Stem Cells Derived From GFAP-hNGF Transgenic Mice: Trophic and Tropic Effects in a Rodent Model of Huntington's Disease", The Journal of Comparative Neurology, 1997; pp. 96-113, vol. 387; Wiley-Liss, Inc.

Kremer, Berry et al., "A worldwide stud of the Huntington's Disease mutation", The New England Journal of Medicine, May 19, 1994; pp. 1403-1406, vol. 330, No. 20; Massachusetts Medical Society.

Loeb, JE et al., "Enhanced Expression of Transgenes from Adeno-Associated Virus Vectors with the Woodchuck Hepatitis Virus Posttranscriptional Regulatory Element: Implication for Gene Therapy", Human Gene Therapy, Sep. 20, 1999; pp. 2295-2305, vol. 10; Mary Ann Liebert, Inc.

Lin, Biaoyang et al., "Structural Analysis of the 5' Region of Mouse and human Huntington Disease Genes Reveals Conservation of Putative Promoter Region and Di- and Trinucleotide Polymorphisms", Genomics, 1995; pp. 707-715, vol. 25; Academic Press, Inc.

Mendel, Itzhack et al., "Interleukin-6 functions in autoimmune encephalomyelitis: a study in gene-targeted mice", Eur. J. Immunol., 1998; pp. 1727-1737, vol. 28.

Murakami, Massaaki et al., "IL-6-Induced Homodimerization of gp130 and Associated Activation of a Tyrosine Kinase", Science, Jun. 18, 1993; pp. 1808-1810, vol. 260.

Naldini, L. et al., "Efficient transfer, integration, and sustained long-term expression of the transgene in adult rat brains injected with a lentiviral vector", Proc. Natl. Acad. Sci., USA, Oct. 1996; pp. 11382-11388, vol. 93.

Novick, Daniella et al., "Enhancement of Interleukin 6 Cytostatic Effect on Human Breast Carcinoma Cells by soluble IL-6 Receptor from urine and reversion by monoclonal antibody", Cytokine, Mar. 1992; pp. 6-1, vol. 4, No. 2.

Novick, D. et al., "Purification of soluble cytokine receptors from normal human urine by ligand-affinity and immunoaffinity chromatography", Journal of Chrommatography, 1990; pp. 331-337, vol. 510; Elsevier Science Publishers B.V., Amsterdam.

Paonessa, Giacomo et al., "Two distinct and independent sites on IL-6 trigger gp130 dimer formation and signaling," The EMBO Journal, 1995; pp. 1942-1951, vol. 14, No. 9.

Pearson, W.R., "Rapid and Sensitive Sequence Comparison with FASTP and FASTA", Methods in Enzymology, 1990; pp. 63-98, vol. 183; Academic Press, Inc.

Pearson, W.R. and Lipman, D.J., "Improved tools for biological sequence comparison", Proc. Natl. Acad. Sci., USA, Apr. 1988; pp. 2444-2448, vol. 85, Biochemistry.

Roberts, Rosalinda C., "Intrastriatal Injections of Quinolinic Acid or Kainic Acid: Differential Patterns of Cell Survival and the Effects of Data Analysis on Outcome", Experimental Neurology, 1993; pp. 274-282, vol. 124; Academic Press, Inc.

Smith and Waterman, "Identification of Common Molecular Subsequences", J. Mol. Biol., 1981; pp. 195-197, vol. 147; Academic Press Inc., London.

Strong, T.V. et al., "Widespread expression of the human and rat Huntington's disease gene in brain and nonneural tissues", Nature Genetics, Nov. 1993; pp. 259-265, vol. 5.

Taga, T. et al., "Interleukin-6 Triggers the Association of its Receptor with a Possible Signal Transducer, gp130", Cell, Aug. 11, 1989; pp. 573-581, vol. 58; Cell Press.

Toulmond, S. et al., "Local infusion of interleukin-6 attenuates the neurotoxic effects of NMDA on rat striatel cholinergic neurons", Neuroscience Letters, 1992; pp. 49-52, vol. 144; Elsevier Scientific Publishers Ireland Ltd.

Ward, L.D. et al., "High Affinity Interleukin-6 Receptor is a Hexameric Complex Consisting of Two Molecules Each of Interleukin-6, Interleukin-6 Receptor, and gp-130", The Journal of Biological Chemistry, Sep. 16, 1994; pp. 23286-23289, vol. 269, No. 37; The American Society for Biochemistry and Molecular Biology, Inc., USA.

Yamada, M. et al., "Interleukin-6 protects cultured rat hippocampal neurons against glutamate-induced cell death", Brain Research, 1994; pp. 173-180, vol. 643; Elsevier Science B.V.

Zufferey, R. et al., "Woodchuck Hepatitis Virus Posttranscriptional Regulatory Element Enhances Expression of Transgenes Delivered by Retroviral Vectors", Journal of Virology, Apr. 1999; pp. 2886-2892, vol. 73, No. 4; American Society for Microbiology.

Bibb, Proc. Natl. Acad. Sci. USA, 97:6809-6814 (2000).

Hansson, Proc. Natl. Acad. Sci. USA, 96:8727-8732 (1999).

Alberts et al., Molecular Biology of the Cell, 3rd Edition, 111-119, 129-130, and 608-609 (1994).

Reddy, Annals of Pharmacology, 34:915-923 (2000).

Lo, Protein Engineering, 11:495-500 (1998).

Strausberg, Current Protocols in Protein Science, 5.6.1-5.6.7 (1995).

Jostock, Journal of Immunological Methods, 22:171-183 (1999).

Heinrich et al., Interleukin-6-type cytokine signalling through the gp130/Jak/STAT pathway, Biochem. J. 334:297-314 (1998).

* cited by examiner

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial
<220> FEATURE:
<223> OTHER INFORMATION: synthetic

<400> SEQUENCE: 1

Glu Phe Gly Ala Gly Leu Val Leu Gly Gly Gln Phe Met
1               5                   10

<210> SEQ ID NO 2
<211> LENGTH: 543
<212> TYPE: PRT
<213> ORGANISM: Artificial Sequence
<220> FEATURE:
<223> OTHER INFORMATION: synthetic

<400> SEQUENCE: 2

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160
```

```
Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Ala Asn Ile Thr Val
            210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Glu Phe Met Pro Val Pro Gly Glu Asp Ser Lys
            355                 360                 365

Asp Val Ala Ala Pro His Arg Gln Pro Leu Thr Ser Ser Glu Arg Ile
            370                 375                 380

Asp Lys Gln Ile Arg Tyr Ile Leu Asp Gly Ile Ser Ala Leu Arg Lys
385                 390                 395                 400

Glu Thr Cys Asn Lys Ser Asn Met Cys Glu Ser Ser Lys Glu Ala Leu
                405                 410                 415

Ala Glu Asn Asn Leu Asn Leu Pro Lys Met Ala Glu Lys Asp Gly Cys
                420                 425                 430

Phe Gln Ser Gly Phe Asn Glu Glu Thr Cys Leu Val Lys Ile Ile Thr
            435                 440                 445

Gly Leu Leu Glu Phe Glu Val Tyr Leu Glu Tyr Leu Gln Asn Arg Phe
            450                 455                 460

Glu Ser Ser Glu Glu Gln Ala Arg Ala Val Gln Met Ser Thr Lys Val
465                 470                 475                 480

Leu Ile Gln Phe Leu Gln Lys Lys Ala Lys Asn Leu Asp Ala Ile Thr
            485                 490                 495

Thr Pro Asp Pro Thr Thr Asn Ala Ser Leu Leu Thr Lys Leu Gln Ala
            500                 505                 510

Gln Asn Gln Trp Leu Gln Asp Met Thr Thr His Leu Ile Leu Arg Ser
            515                 520                 525

Phe Lys Glu Phe Leu Gln Ser Ser Leu Arg Ala Leu Arg Gln Met
            530                 535                 540
```

USE OF IL-6/IL-6 CHIMERA IN HUNTINGTON'S DISEASE

CROSS-REFERENCE TO RELATED APPLICATIONS

The present application is a continuation of Ser. No. 11/622,284, filed Jan. 11, 2007, which is a continuation of Ser. No. 10/380,427, now abandoned, which is a 371 national sage application of PCT/EP01/10442, filed Sep. 10, 2001. The entire contents of these applications are incorporated herein by reference.

FIELD OF THE INVENTION

The present invention is in the field of Huntington's disease (HD). In particular, it relates to the use of an IL-6R/IL-6 chimera for the manufacture of a medicament for the treatment and/or prevention of Huntington's disease.

BACKGROUND OF THE INVENTION

Huntington's Disease is an inherited, autosomal dominant neurological disease. It is uncommon, affecting approximately 1 in 10000 individuals (Breighton and Hayden 1981). The disease does not usually become clinically apparent until the fifth decade of life, and results in psychiatric disturbance, involuntary movement disorder, and cognitive decline associated with inexorable progression to death, typically 17 years following onset.

The gene responsible for Huntington's disease is called huntingtin. It is located on chromosome 4p, presenting an effective means of preclinical and antenatal diagnosis. The genetic abnormality consists in an excess number of tandemly repeated CAG nucleotide sequences.

The huntingtin gene is ubiquitously expressed (Strong et al. 1993) and conserved across a wide range of species (Lin et al., 1994). Structural analysis of its promoter region is consistent with it being a housekeeping gene (Lin et al., 1995). The huntingtin gene encompasses 67 exons, spans over 200 kb (Ambrose et al., 1994) and is associated with two transcripts of 10.3 kb and 13.6 kb, differing with respect to their 3' untranslated regions (Lin et al., 1993). Both messages are predicted to encode a 348 kilodalton protein containing 3144 amino acids. In addition, the huntingtin gene encompasses a highly polymorphic CAG repeat, which varies in number from 8 to 35 in normal individuals (Kremer et al., 1994). CAG expansion beyond 36 CAG repeats is seen in persons with Huntington's disease.

The increase in size of the CAG repeat in persons with Huntington's disease shows a highly significant correlation with age of onset of clinical features. This association is particularly striking for persons with juvenile onset Huntington's disease who have very significant expansion, usually beyond 50 repeats. The CAG repeat length in Huntington's disease families does exhibit some instability that is particularly marked when children inherit the huntingtin gene from affected fathers.

In HD, it is not known how this widely expressed gene results in selective neuronal death. Furthermore, sequence analysis revealed no obvious homology to other known genes and no structural motifs or functional domains were identified which clearly provide insights into its function. In particular, the question of how these widely expressed genes cause selective neuronal death remains unanswered.

The major site of pathology in HD is the striatum, where up to 90% of the neurons may be depleted. Within the striatum there is a selective loss of certain neuronal populations. Striatal medium-sized spiny neurons, which contain the neurochemical markers gamma-aminobutyric acid (GABA), substance P, dynorphin, and enkephalin are preferentially affected. In contrast, medium-sized aspiny neurons containing the neuropeptides somatostatin and neuropeptide Y, and large aspiny neurons containing choline acetyltransferase (ChAT) activity, are spared (despite an overall loss of ChAT activity). Dopaminergic and serotonergic afferent projections are also spared. (Beal et al, 1991).

The impaired cognitive functions and eventual dementia may be due either to the loss of cortical neurons or to the disruption of normal activity in the cognitive portions of the basal ganglia, namely the dorsolateral prefrontal and lateral orbitofrontal circuits. The characteristic chorea is believed to be caused by the neuronal loss in the striatum, although a reduction in subthalamic nucleus activity may also contribute to it. Normally a balance is maintained among the activities of three biochemically distinct but functionally interrelated systems: (1) the nigrostriatal dopaminergic system; (2) the intrastriatal cholinergic neurons; and (3) the GABA-ergic system, which projects from the striatum to the globus pallidus and substantia nigra. An imbalance anywhere in the dopamine, acetylcholine, or GABA systems can cause involuntary movements. Both choline acetyltransferase, the enzyme required for the formulation of acetylcholine, and glutamic acid decarboxylase, the enzyme required to synthesize GABA, are markedly decreased in the striatum of patients with HD. These enzyme deficits are consistent with the clinical observation that choreic movements worsen in patients with HD following administration of L-DOPA.

Glutamate-induced neuronal cell death is believed to contribute to Huntington's disease. Glutamate is the principal excitatory transmitter in the brain. It excites virtually all central neurons and is present in the nerve terminals in extremely high concentrations ($10^{-3}$ M). Glutamate receptors are divided into four types (named after their model agonists): kainate receptors, N-methyl-D-aspartate (NMDA) receptors, α-amino-3-hydroxy-5-methyl-4-isoxazolepropionate (AMPA) receptors, and metabolotrophic receptors. Many normal synaptic transmission events involve glutamate release.

Glutamate can also induce neurotoxicity and neuronal death at high levels (Choi, 1988). The mechanism of cell death occurs primarily by the persistent action of glutamate on the N-methyl-D-aspartate (NMDA) type of glutamate receptors and the resulting excessive influx of $Ca^{2+}$. The excessive $Ca^{2+}$ mobilizes active $Ca^{2+}$-dependent proteases and activates phospholipase A2, which in turn liberates arachidonic acid, leading to the production of substances causing inflammation and free radicals that can trigger further destructive events. These toxic changes produced by glutamate, called glutamate excitotoxicity, are believed to be the cause of cell damage and death after acute brain injury such as stroke or excessive convulsions. It has been suggested that excitotoxicity may be involved in brain ischemia, Alzheimer's disease and HD (Greenamyre et al, 1985; Choi et al, 1988).

Several animal models mimicking HD pathology have been set up. Injection of glutamate receptor agonists into rat striatum can produce a pattern of neuronal cell loss similar to HD. Although the majority of the neurons within the actual injection site die, there is a surrounding gradual transition zone that exhibits selective cell death. Initial studies with kainic acid (KA)-induced lesions showed a striking resemblance to HD. KA is isolated from the seaweed Diginea simplex and is not found in the mammalian brain. Intrastriatal injections of KA result in neuronal loss and gliosis, with reductions in markers of intrinsic striatal neurons, yet a preservation of dopaminergic afferents. These KA-induced lesions, however, are an imperfect model of HD because they result in a significant depletion of somatostatin levels and a loss of somatostatin neurons. Lesions produced by NMDA receptor agonists such as quinolinic acid (QA) provide a better model of HD, because they result in relative sparing of somatostatin and neuropeptide Y levels, despite significant depletions of both GABA and substance P levels. Long-term (6 months to 1 year) follow-up of QA lesions reveals increases in somatostatin and neuropeptide Y and in serotonin and in 5-hydroxyindoleacetic acid (HIAA), which are similar to the findings in actual HD patients. Chronic QA lesions therefore closely resemble the neurochemical features of HD (Beal et al, 1991.) Others have confirmed that QA-induced injury of the striatum can resemble the histopathology of HD (See, e.g., Roberts et al, 1993).

These animal models have been extensively used to develop strategies that may be relevant for the treatment of HD, such as cell replacement and neuroprotective approaches. A significant rescue of degenerating GABAergic neurons was observed following the grafting of fetal striatal cells or the administration of neurotrophic factors in QA-lesioned rats (Bemelmans et al. 1999).

Further neurochemical abnormalities have been identified in HD, for example reduced levels of choline acetyltransferase and gamma aminobutyric acid in the basal ganglia. These changes are presumable secondary to the primary neuronal loss.

There is presently no cure for Huntington's disease. The choreic movements and agitated behaviors may be suppressed, usually only partially, by antipsychotics (e.g., chlorpromazine 100 to 900 mg/day per os or haloperidol 10 to 90 mg/day per os) or reserpine begun with 0.1 mg/day per os and increased until adverse effects of lethargy, hypotension, or parkinsonism occur. Therapeutic strategies to replace brain GABA stores have been ineffective. Experimental therapies aim to reduce glutamatergic neurotransmission via the N-methyl-D-aspartate receptor and bolster mitochondrial energy production. Long-term clinical trials are needed to assess these therapies All treatment presently available focuses on addressing the disease's symptoms, preventing associated complications and providing support and assistance to the patient. For those diagnosed with HD, physicians often prescribe various medications to help control emotional and movement problems. Benzodiazepines may alleviate choreic movements, and antipsychotic drugs may help control hallucinations, delusions or violent outbursts. If the patient suffers from depression, the physician may prescribe antidepressants. Tranquilizers can be used to treat anxiety, and lithium may be prescribed for patients who exhibit pathological excitement or severe mood swings. Other medications may be prescribed for the severe obsessive-compulsive behaviors some individuals with HD develop.

Therefore, there is an unmet need for a medicament, pharmaceutical compositions and methods useful for the treatment of Huntington's disease. Such medicaments, pharmaceutical compositions and methods will ideally stop the progression of the degenerative disease and even promote regeneration of the damaged neurons, without severe adverse side effects.

Several neurotrophic factors have been tested in animal models of HD so far (Andersen et al, 1996). Brain-derived growth factor (BDNF), nerve growth factor (NGF) or neurotrophin-3 (NT-3) did not result in protection of striatal neurons from QA induced cell death. Ciliary neurotrophic factor (CNTF) had some protective effect in a monkey model of HD (Emerich et al, 1997).

Some neuroprotective strategies using gene therapeutic approaches have been suggested. These approaches rely on the development of effective delivery systems leading to robust expression of the transgene over extended periods of time and the presence of therapeutic protein in large area of the striatum. The transplantation of genetically engineered cells, the implantation of encapsulated cells releasing neurotrophic factors and more recently an in vivo gene therapy approach with an adenoviral vector have been tested (Emerich et al. 1996, Bemelmans et al. 1999). HIV-1-derived lentiviral vectors have recently emerged as a promising gene delivery system in the CNS (Naldini et al. 1996a; Klimatcheva et al. 1999). Since 1996, significant efforts have been dedicated to increase the safety of the system and to define the minimal genetic information required for the transduction HIV-1 vectors.

To minimize the risk of emergence of replication-competent recombinants so-called SIN (self inactivating) vectors were developed. The SIN design results in the deletion of the U3 region in the long terminal repeat (LTR) from the transfer vector, removing the major part of the viral transcriptional elements prior to integration. This modification not only reduces the risk of appearance of replication-competent viruses through recombination, but also eliminates transcriptional interference between the LTR and the internal promoter, and minimizes the chance that genes adjacent to the vector integration site become activated (Déglon et al., 2000).

This expression vector system has been previously demonstrated to lead to a high and consistent transduction of neuronal cells with a SIN expressing the LacZ reporter gene in mice, rats and primates (Bensadoun et al. 2000; Déglon et al. 2000; Kordower et al. 1999). In addition, the presence of the post-transcriptional element from the woodchuck hepatitis virus (Zufferey et al. 1999) was shown to result in a 3-4 fold increase of the transgene expression level (Déglon et al, 2000) similarly to what was observed in adeno-associated viruses (Loeb et al. 1999).

Experiments on the effects of a cytokine, interleukin-6 (IL-6), on cells of the central and peripheral nervous system indicate that IL-6 may have protective effects on neuronal cells as well as some impact on inflammatory neurodegenerative processes (Gadient and Often, 1997, Mendel et al, 1998). IL-6 was found to prevent glutamate-induced cell death in hippocampal (Yamada et al., 1994) as well as in striatal (Toulmond et al., 1992) neurons. The IL-6 mechanism of neuroprotection against toxicity elicited by NMDA, the selective agonist for NMDA subtype of glutamate receptors, is still unknown. In fact IL-6 was found to enhance the NMDA-mediated intracellular calcium elevation. In transgenic mice expressing high levels of both human IL-6 and human soluble IL-6R (sIL6-R), an accelerated nerve regeneration was observed following injury of the hypoglossal nerve as shown by retrograde labeling of the hypoglossal nuclei in the brain (Hirota et al, 1996). Recently, there has been some evidence that IL-6 is implied in a neurological disease, the demyelinating disorder Multiple Sclerosis (MS) (Mendel et al., 1998). Mice lacking the IL-6 gene were resistant to the experimental induction of the disease.

Interleukin-6 (IL-6) is a well known cytokine whose biological activities are mediated by a membrane receptor system comprising two different proteins one named IL-6 Receptor (IL-6R or gp80) and the other gp130 (reviewed by Hirano et al, 1994). Soluble forms of IL-6R (sIL-6R), corresponding to the extracellular domain of gp80, are natural products of the human body found as glycoproteins in blood and in urine (Novick et al, 1990, 1992). An exceptional property of sIL-6R molecules is that they act as potent agonists of IL-6 on many cell types including human cells (Taga et al, 1989; Novick et al, 1992). Even without the intracytoplasmic domain of gp80, sIL-6R is still capable of triggering the dimerization of gp130 in response to IL-6, which in turn mediates the subsequent IL-6-specific signal transduction and biological effects (Murakanni et al, 1993). sIL-6R has two types of interaction with gp130 both of which are essential for the IL-6 specific biological activities (Halimi et al., 1995), and the active IL-6 receptor complex was proposed to be a hexameric structure formed by two gp130 chains, two IL-6R and two IL-6 ligands (Ward et al., 1994; Paonessa et al, 1995).

Chimeric molecules linking the soluble IL-6 receptor and IL-6 together have been described (Chebath et al., 1997. Fischer et al., 1997. WO 99/02552 and WO 97/32891). They have been designated IL-6R/IL-6 chimera and Hyper-IL-6, respectively. The chimeric IL-6R/IL-6 molecules were generated by fusing the entire coding regions of the cDNAs encoding the soluble IL-6 receptor (sIL-6R) and IL-6. Recombinant IL-6R/IL-6 chimera was produced in CHO cells (Chebath et al, 1997, WO99/02552). The IL-6R/IL-6 binds with a higher efficiency to the gp130 chain in vitro than does the mixture of IL-6 with sIL-6R (Kollet et al, 1999).

The IL-6R/IL-6 chimera has further been shown to induce the expression of myelin basic protein (MBP) and Po gene products MBP and Po RNAs and proteins in cultures of dorsal root ganglia (DRG) from 14 day old mouse embryos (Haggiag et al., 1999). MBP and Po proteins are normally induced during the final postnatal maturation of Schwann cells, and they are re-induced during nerve regeneration. The IL-6R/IL-6 chimera may thus have a role in neural myelination and regeneration.

SUMMARY OF THE INVENTION

In accordance with the present invention it has been found that the administration of an IL-6R/IL-6 chimera has a highly beneficial effect on the development of Huntington's disease. In particular, the administration of IL-6R/IL-6 chimera has been shown to lead to a significant protection from striatal neuronal cell loss as well as to an amelioration of behavioral defects in an established animal model of HD.

The invention therefore relates to the use of an IL-6R/IL-6 chimera, a mutein, isoform, fused protein, functional derivative, active fraction, circularly permutated derivative or salt thereof, for the manufacture of a medicament for the treatment and/or prevention of Huntington's disease. The invention further relates to the use of cells and vectors comprising an IL-6R/IL-6 chimera, a mutein, isoform, fused protein, active fraction or circularly permutated derivative thereof, for the manufacture of a medicament for the treatment and/or prevention of Huntington's disease. Corresponding pharmaceutical compositions and methods of treatment are further objects of the present invention.

DETAILED DESCRIPTION OF THE INVENTION

Figure 1:
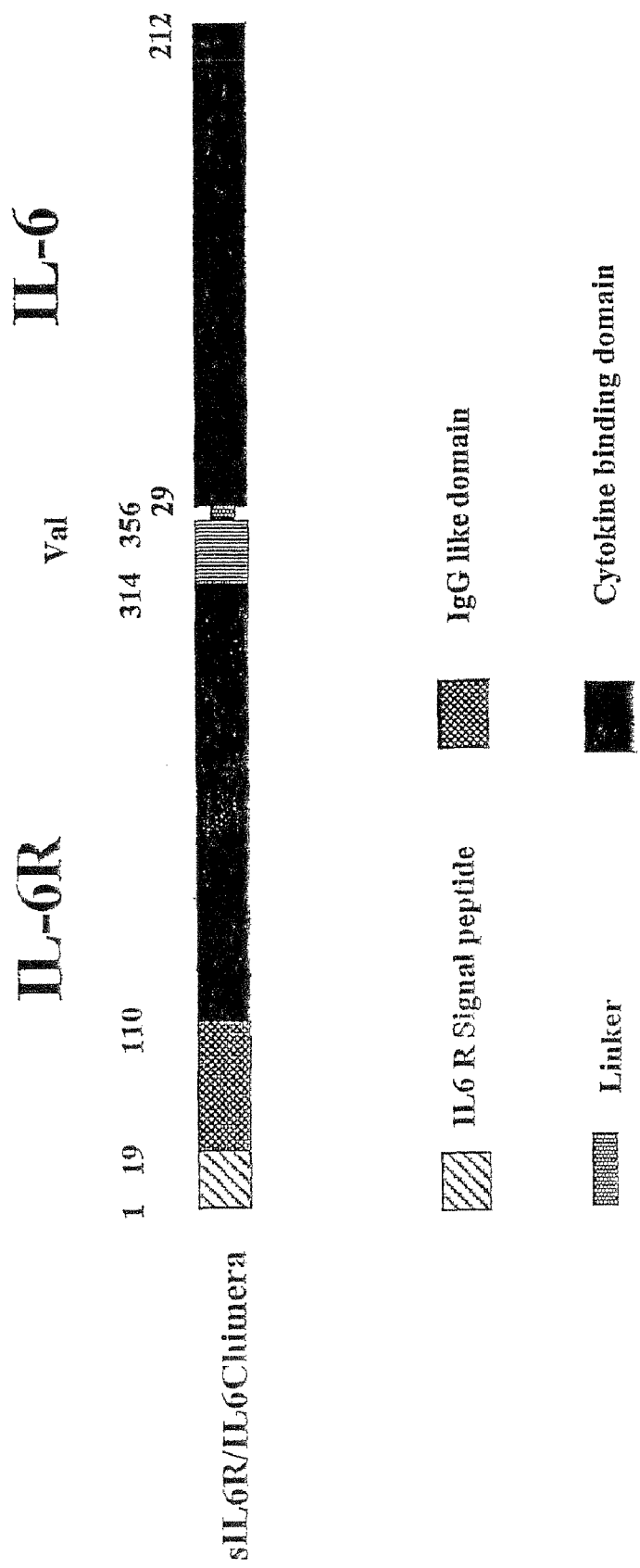
FIG. 1 is a schematic drawing illustrating the IL-6R/IL-6 chimera protein structure.

The invention is based on the finding that the administration of an IL-6R/IL-6 chimera led to a significant protection from cell death of striatal GABAergic neurons as well as to an amelioration of behavioral defects in an established animal model of Huntington's Disease (HD).

The invention therefore relates to the use of a IL-6R/IL-6 chimera, a mutein, isoform, fused protein, functional derivative, active fraction, circularly permutated derivative or salt thereof for the manufacture of a medicament for the treatment and/or prevention of Huntington's disease.

An "IL-6R/IL-6 chimera" (also called "IL-6R/IL-6" or "IL-6 chimera"), as used herein, is a chimeric molecule comprising a soluble part of the interleukin-6 receptor fused to all or a biologically active fraction of interleukin-6. The moieties of the chimeric protein can be fused directly, or they can be linked by any suitable linker, such as a disulfide bridge or a polypeptide linker. The linker may be a short linker peptide which can be as short as 1 to 3 amino acid residues in length or longer, for example, 13 or 18 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO:1) introduced between the amino acid sequence of the soluble IL-6 receptor and the IL-6 sequence. Examples of IL-6R/IL-6 chimeric molecules are known in the art and have been described in detail e.g. in WO 99/02552 or WO 97/32891. One specific example of such a chimera with an E-F-M tripeptide is in FIG. 3 of WO 99/02552 (SEQ ID NO:2). Residues 20-356 are the sIL-6R sequence (residues 1-19 being the signal sequence), residues 357-359 are the tripeptide linker, and residues 360-543 are the IL-6 sequence.

The term "treating" as used herein should be understood as inhibiting, attenuating, ameliorating or reversing any or all symptoms or cause(s) of Huntington's disease, as well as symptoms or diseases accompanying HD, and in particular the neuroanantomical and behavioral changes associated with the disease.

The term "preventing" as used herein should be understood as preventing any or all symptoms or cause(s) of Huntington's disease, as well as symptoms or diseases accompanying HD, and in particular the neuroanantomical and behavioral changes associated with the disease.

The term "Huntington's disease" or "HD", as used herein, is also called Huntington's Chorea, Chronic Progressive Chorea or Hereditary Chorea, and is an autosomal dominant disorder characterized by choreiform movements and progressive intellectual deterioration. The disease, as well as its causes, symptoms and current therapies have been described in detail in the "Background of the Invention".

The invention provides for a new possibility of treating and/or preventing HD, a so far practically untreatable disorder of the brain. The present invention presents a substantial progress, since the medicaments presently used mainly aimed at preventing associated complications and providing support and assistance to the patient, thus not directly attacking one of the assumed causes underlying the disease, i.e. neuronal cell loss in the striatum. Compared to another protein suggested to be useful in the treatment of HD, namely CNTF (Ciliary Neurotrophic Factor), IL-6R/IL-6 chimera exhibits an even more pronounced beneficial effect in the same animal model of HD. As shown in the examples below. IL-6R/IL-6 exhibited an effect which was superior to the effect shown by IL-6, both in terms of neuroprotection in the striatum and with regard to amelioration of the behavioral aberrations tested in an established animal model of HD.

As used herein the term "muteins" refers to analogs of an IL-6R/IL-6 chimera, in which one or more of the amino acid residues of the naturally occurring components of IL-6R/IL-6 are replaced by different amino acid residues, or are deleted, or one or more amino acid residues are added to the original sequence of an IL-6R/IL-6, without changing considerably the activity of the resulting products as compared with the original IL-6R/IL-6. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes an IL-6R/IL-6, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook. J. C. Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SOS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of an IL-6R/IL-6, such as to have substantially similar, or even better, activity to IL-6R/IL-6.

One characteristic activity of IL-6R/IL-6 is its capability of binding to gp130. An ELISA type assay for measuring the binding of IL-6R/IL-6 to gp130 has been described in detail in example 7 on page 39 of WO 99/02552, which is fully incorporated by reference herein. As long as the mutein has substantial binding activity to gp130, it can be considered to have substantially similar activity to IL-6R/IL-6. Thus, it can be determined whether any given mutein has at least substantially the same activity as IL-6R/IL-6 by means of routine experimentation comprising subjecting such a mutein, e.g., to a simple sandwich binding assay to determine whether or not it binds to an immobilized gp130, as described in example 7 of WO 99/02552.

In a preferred embodiment, any such mutein has at least 40% identity or homology with the sequence of IL-6R/IL-6 comprised in WO 99/02552. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Muteins of IL-6R/IL-6, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-6R/IL-6 may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |

TABLE 3-continued

Most Preferred Groups of Synonymous Amino Acids

| Amino Acid | Synonymous Group |
|---|---|
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-6R/IL-6 polypeptides, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

The term "fused protein" refers to a polypeptide comprising an IL-6R/IL-6, or a mutein or fragment thereof, fused with another protein, which, e.g., has an extended residence time in body fluids. An IL-6R/IL-6, may thus be fused to another protein, polypeptide or the like, e.g., an immunoglobulin or a fragment thereof.

"Functional derivatives" as used herein cover derivatives of IL-6R/IL-6, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-6R/IL-6, and do not confer toxic properties on compositions containing it.

These derivatives may, for example, include polyethylene glycol side-chains, which may mask antigenic sites and extend the residence of an IL-6R/IL-6 in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

An "active fraction" according to the present invention may e.g. be a fragment of IL-6R/IL-6. The term fragment refers to any subset of the molecule, that is, a shorter peptide which retains the desired biological activity. Fragments may readily be prepared by removing amino acids from either end of the IL-6R/IL-6 molecule and testing the resultant fragment for its properties to bind to gp130. Proteases for removing one amino acid at a time from either the N-terminal or the C-terminal of a polypeptide are known, and so determining fragments which retain the desired biological activity involves only routine experimentation.

As active fractions of an IL-6R/IL-6, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to gp130.

The term "salts" herein refers to both salts of carboxyl groups and to acid addition salts of amino groups of the IL-6R/IL-6 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IL-6R/IL-6, i.e., the ability to bind to gp130.

In a preferred embodiment of the invention, the IL-6R/IL-6 chimera is glycosylated at one or more sites.

A glycosylated form of an IL-6R/IL-6 chimera has been described in WO 99/02552 (PCT/IL98/00321), which is the chimeric molecule highly preferred according to the invention. The IL-6R/IL-6 chimera described therein is a recombinant glycoprotein which was obtained fusing the entire coding sequence of the naturally-occurring soluble IL-6 receptor δ-Val (Novick et al., 1990) to the entire coding sequence of mature naturally-occurring IL-6, both from human origin.

The IL-6R/IL-6 chimera may be produced in any adequate eukaryotic or procaryotic cell type, like yeast cells, insect cells, bacteria, and the like. It is preferably produced in mammalian cells, most preferably in genetically engineered CHO cells as described in WO 99/02552. Whilst the protein from human origin is preferred, it will be appreciated by the person skilled in the art that a similar fusion protein of any other origin may be used according to the invention, as long as it retains the biological activity described herein.

In a further embodiment of the invention, the IL-6R/IL-6 chimera is not glycosylated. Advantageously, the chimeric molecule can then be produced in bacterial cells, which are not capable of synthesizing glycosyl residues, but usually have a high yield of produced recombinant protein.

In yet a further embodiment, the IL-6R/IL-6 chimera further comprises an immunoglobulin fusion, i.e. the IL-6R/IL-6 according to the invention is fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of the IL-6R/IL-6 chimera. The resulting fusion protein ideally has improved properties, such as an extended residence time in body fluids (half-life), increased specific activity, increased expression level, or facilitated purification of the fusion protein.

In a preferred embodiment, the IL-6R/IL-6 chimera is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero-homomultimeric.

Functional derivatives of IL-6R/IL-6 chimera may be conjugated to polymers in order to improve the properties of the protein, such as the stability, half-life, bioavailability, tolerance by the human body, or immunogenicity.

Therefore, a preferred embodiment of the invention relates to a functional derivative of the IL-6R/IL-6 chimera comprising at least one moiety attached to one or more functional groups which occur as one or more side chains on the amino acid residues.

A highly preferred embodiment relates to an IL-6R/IL-6 linked to Polyethlyenglycol (PEG). PEGylation may be carried out by known methods, such as the ones described in WO 92/13095, for example.

The IL-6R/IL-6 chimera may be delivered to the brain in any adequate formulation. Preferably, it may be delivered in form of cells expressing and/or secreting an IL-6R/IL-6 chimera, a mutein, fused protein, active fraction or circularly permutated derivative thereof. As illustrated in the examples below, cells expressing and secreting IL-6R/IL-6 chimera in sufficient amounts have been generated by transfection using a suitable expression vector.

The invention therefore further relates to the use of a cell expressing IL-6R/IL-6 chimera, a mutein, fused protein, active fraction or circularly permutated derivative thereof, for manufacture of a medicament for the treatment and/or prevention of Huntington's disease. The cells may be administered in any suitable form. However, a polymer-encapsulated IL-6R/IL-6 chimera expressing, and preferably secreting cell, is a highly preferred mode of delivery of IL-6R/IL-6 chimera. The encapsulation procedure is described in detail e.g. by Emerich et al (1994) or U.S. Pat. No. 5,853,385. Suitable cell lines and stable expression systems are well known in the art.

The delivery of IL-6R/IL-6 chimera may also be carried out using a vector, such as an expression vector, comprising the coding sequence or an IL-6R/IL-6 chimera, a mutein, fused protein, active fraction or circularly permutated derivative thereof. The vector comprises all regulatory sequences needed for expression of the desired protein in the human body, preferably in the brain, more preferably in the striatum. Regulatory sequences for expression vectors are known by the person skilled in the art. The invention thus also relates to the use of a vector comprising the coding sequence of IL-6R/IL-6 chimera for manufacture of a medicament for the treatment and/or prevention of Huntington's disease.

Any expression vector known in the art may be used according to the invention. However, as shown in the examples below, a lentivirally derived vector was particularly useful for the delivery of IL-6R/IL-6 chimera directly into the striatum. Therefore, a highly preferred embodiment of the invention relates to the use of a lentiviral vector as an expression vector for the expression of IL-6R/IL-6 chimera, a mutein, fused protein, active fraction or circularly permutated derivative thereof. Such lentiviral vectors are known in the art. They are specifically described e.g. in Kordower et al. (1999) or DegIon et al. (2000).

It is a further object of the present invention to provide a pharmaceutical composition comprising IL-6R/IL-6 chimera, a mutein, fused protein, functional derivative, active fraction, circularly permutated derivative or salt thereof, optionally together with one or more pharmaceutically acceptable carriers, diluents or excipients, for the treatment and/or prevention of Huntington's disease.

The invention further relates to a pharmaceutical composition comprising a cell expressing IL-6R/IL-6 chimera, and to a pharmaceutical composition comprising an expression vector, in particular a lentiviral gene therapy vector expressing IL-6R/IL-6 chimera, optionally together with one or more pharmaceutically acceptable carriers, diluents or excipients, for the treatment and/or prevention of Huntington's disease.

The definition of "pharmaceutically acceptable" is meant to encompass any carrier, which does not interfere with effectiveness of the biological activity of the active ingredient and that is not toxic to the host to which it is administered. For example, for parenteral administration. IL-6R/IL-6 chimera may be formulated in a unit dosage form for injection in vehicles such as saline, dextrose solution, serum albumin and Ringer's solution.

The IL-6R/IL-6 chimera can be administered to a patient in need of administration thereof in a variety of ways. The routes of administration include intracranial, intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the IL-6R/IL-6 chimera is administered to the patient (e.g. via a vector) which causes the IL-6R/IL-6 chimera to be expressed and secreted in vivo. In addition the IL-6R/IL-6 chimera can be administered together with other components of biologically active agents such as pharmaceutically acceptable surfactants, excipients, carriers, diluents and vehicles.

For parenteral (e.g. intravenous, subcutaneous, intramuscular) administration, IL-6R/IL-6 chimera can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

It is a further object of the present invention to provide for a method for treating and/or preventing Huntington's disease, comprising administering to a patient in need thereof an effective amount of IL-6R/IL-6 chimera, a mutein, fused protein, functional derivative, active fraction, circularly permutated derivative or salt thereof optionally together with a pharmaceutically acceptable carrier.

An "effective amount" refers to an amount of the active ingredients that is sufficient to affect the course and the severity of the diseases described above, leading to the reduction or remission of such pathology. The effective amount will depend on the route of administration and the condition of the patient.

The dosage administered, as single or multiple doses, to an individual will vary depending upon a variety of factor, including IL-6R/IL-6 chimera pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

A method for treating Huntington's disease, comprising administering to a patient in need thereof an effective amount of a cell expressing IL-6R/IL-6 chimera, a mutein, fused protein, active fraction or circularly permutated derivative thereof, or comprising administering to a patient in need thereof an expression vector comprising the coding sequence of IL-6R/IL-6 chimera, a mutein, fused protein, active fraction or circularly permutated derivative thereof, are further objects of the present invention.

In a preferred embodiment of the invention, the expression vector is a gene therapy vector. The use of a viral vector, in particular a lentiviral vector, is highly preferred.

The present invention will now be described in more detail in the following non-limiting examples and the accompanying drawings.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Materials and Methods

IL-6R/IL-6 Chimera

The cDNA sequences encoding for the soluble IL-6 receptor (natural form of sIL-6 found in urine, Oh et al., 1997) have been fused with those encoding for mature IL-6. Sequences for 3 bridging amino acids (EFM) were also present. The fused gene was inserted in an expression vector under the control of CMV promoter and introduced into CHO cells. A production process has been developed and the resulting recombinant protein has been purified by immunopurification using an anti-IL-6R monoclonal antibody. The purified IL-6 chimera has been shown to be glycosylated and to display an apparent MW of 85,000.

FIG. 1 schematically shows the composition of the IL-6R/IL-6 chimera protein. The mature protein comprises 524 amino acids.

A protein produced and purified as outlined above is suitable to be administered according to the invention.

Lentiviral Vector Production

The cDNAs encoding for a nuclear-localized β-galactosidase (LacZ), the human IL-6 (Genbank M14584: 64-824 bp) and the human IL-6R/IL-6 chimera (Genbank NM000565: 415-1508 bp; Genbank M14584: 148-702 bp) (Haggiag et al. 1999; Katz et al., 1998) were cloned into the SIN-W-PGK transfer vector (Déglon et al., 2000). Three bridging amino acids (Glu-Phe-Met) were present at the junction of the IL-6 and IL-6R. The viral particles were produced as previously described (Hottinger et al., 2000). LacZ-, IL-6- and IL-6R/IL-6-expressing viruses were resuspended in phosphate buffered saline (PBS)/1% bovine serum albumin (BSA) and matched for particle content (250000 ng p24 antigen/ml as measured by ELISA assay).

In Vivo Experiments

Adult female Wistar rats (Iffa-Credo, France) weighing 180-200 g were used. The animals were housed in a temperature controlled room that was maintained on a 12 hr light/dark cycle. Food and water were available ad libitum. The experiments were carried out in accordance with the European Community Council directive (86/609/EEC) for the care and use of laboratory animals.

a) Injection of the Lentiviruses

The concentrated viral stocks were defrosted and then resuspended by repeated pipetting. Two microliters of IL-6, IL-6R/IL-6, or LacZ-expressing lentiviral vectors were stereotaxically injected into the striatum of animals (n=6 per group) that had been anesthetized with pentobarbital (45 mg/kg, i.p.) using a Hamilton syringe with a 33 gauge blunt tip needle (Hamilton, Reno, Nev.). The stereotaxic coordinates for the injection were: 1.0 mm rostral to bregma; 2.2 mm lateral to midline (LM); 5 mm ventral from the dural surface. The suspension was injected at 0.2 µl/min and the needle was left in place for 5 min. The skin was closed using a 6-0 Vicryl® suture (Ethicon. Johnson and Johnson, Brussels). The animals were allowed to recover for three weeks prior to quinolinic acid injection.

b) Quinolinic Acid Lesion

Quinolinic acid (180 nmol, Sigma Chemical, St. Louis, USA) was dissolved in 2 M NaOH, the pH was adjusted to 7.4 and the volume completed with PBS at pH 7.4. The animals were anesthetized with pentobarbital (45 mg/kg) and received an intrastriatal injection of 1 µl of quinolinic acid (180 nmol) using the following coordinates: 1.0 rostral to bregma; 3.2 mm lateral to midline (LM); 5 mm ventral from the dural surface. The toxin was injected over 1 min, and the needle was left in place for an additional 3 min.

Behavioral Analysis

Apomorphine-induced rotational asymmetry was measured twice before the injection of the virus. Animals were injected subcutaneously with 1.0 mg/kg apomorphine (Amino A G, Neunhof, Switzerland) and placed into a test chamber (Rotoscan, Rotometer v5.06, Omnitech Instruments, Columbus, USA) for a 3 min habituation period followed by a 45 min test session. Rotations were defined as complete 360° ipsilateral turns and were reported as the net difference between ipsilateral and contralateral rotations. Animals that did not display spontaneous turning behavior (less than 40 turns per 45 min) were selected. The animals were tested 1 and 2 weeks after the injection of the virus and 5, 9 and 13 days after QA administration. Results are expressed as the net difference between the total number of turns before and after the administration of QA. Ipsilateral turns were counted as positive turns, whereas contralateral turns were counted as negative turns.

IL-6 and IL-6R/IL-6 Chimera ELISA Assays

The in vivo synthesis of IL-6 and IL-6R/IL-6 chimera was determined from punches (2.8×2 mm) taken around the injection sites and from the non-injected hemispheres of control rats (n=5 per group). The samples were sonicated in 500 µl PBS containing a mixture of protease inhibitors (pronase, thermolysin, chymotrypsin, trypsin, papain; Roche Pharma, Reinach, Switzerland). IL-6 production was quantified by ELISA according to the supplier's recommendations (IL-6 EASIA-45 min; Biosource Europe S A, Nivelles, Belgium).

The production of IL-6R/IL-6 chimera was determined as follows. Ninety-six well plates (Maxisorb; NUNC, LifeTechnologies AG, Basel, Switzerland) were coated overnight with 100 µl of 1 µg/ml anti-IL-6R monoclonal antibodies (clone 34.1 provided by Serono International) diluted in PBS. The blocking step was performed with 2% I-block (Tropix, Bedford, Mass., USA) in PBS for 1 hr at 37° C. Samples (100 µl/well) were diluted in 1% I-block, 0.1% Tween 20 and 5% mouse serum in PBS and incubated for 1 hr at 37° C. The secondary antibodies (IgG to sIL6-R 3466, provided by Serono International) were diluted 1/1000 in 1% I-block and 0.1% Tween 20 in PBS and were then incubated (100 µl/well) for 1 hr at 37° C. Goat anti-rabbit antibodies conjugated to HRP (provided by Serono International; dilution 1/5000 in PBS, 1% I-block and 0.1% Tween 20) were incubated for 1 hr at 37° C. The presence of the IL-6R/IL-6 chimera was revealed by use of the TMB kit (Roche Pharma, Reinach, Switzerland). The optical density was measured at 450 nm.

Histological Processing

Two weeks after QA lesion, the animals were given a sodium pentobarbital overdose and transcardially perfused with saline and 4% paraformaldehyde. The brains were removed and post-fixed in 4% paraformaldehyde for approximately 24 hrs and finally cryoprotected in 25% sucrose/0.1 M phosphate buffer for 48 hrs. The brains were frozen in dry ice and 25 µm coronal sections were cut on a sliding microtome cryostat (Cryocut 1800, Leica Microsystems, Nußloch, Germany) at −20° C. Slices throughout the entire striatum were collected and stored in 48 well trays (Costar, Cambridge, Mass.) as free-floating sections in PBS supplemented with 0.12 µM sodium azide. The trays were stored at 4° C. until immunohistochemical processing.

The samples were processed by immunohistochemistry for dopamine and cAMP-regulated phosphoprotein of a molecular mass of 32 kDa (DARPP-32), choline acetyltransferase (ChAT) (Roche Pharma, Reinach, Switzerland), IL-6 (R&D system Abington, UK) and glial fibrillary acidic protein (GFAP) (Sigma-Genosys Ltd, Cambridge, UK). Enzymatic staining for NADPH-diaphorase (NADPH-d) was performed as previously described (Ellison et al., 1987). For immunohistochemical stainings, endogenous peroxidase activity was quenched with 0.1% diphenylhydrazine/PBS (37° C./30') and washed 3 times in PBS. Free-floating sections were incubated overnight in 5% normal goat serum (NGS, Dako Diagnostics, Switzerland)/0.1 M phosphate buffered saline at 4° C., followed by an overnight reaction with the respective antibodies: DARPP-32 (1:20 000), ChAT (1:50), IL-6 (1:200), GFAP (1:400) diluted in PBS/1% NGS solution. After 3 washes the sections were incubated with the corresponding biotinylated secondary antibodies (Vector, 1:200) for 2 hrs at room temperature, and bound antibodies were visualized by the ABC system (Vectastain ABC Kit, Vector Laboratories, West Grove, USA) with 3,3' diaminobenzidin (DAB Metal Concentrate, Pierce, Rockford, Ill., USA) as chromogen. The sections were dehydrated by passing twice through ethanol and toluol and covered with Merckoglas® coverslips.

Image Analysis

The QA lesions were analyzed by digitizing between 9 and 12 DARPP-32-stained sections per animal (200 μm between each section) with a slide scanner and by quantifying the optical density with an image analysis public domain program (NIH-Image. Version 1.6.1, National Institutes of Health, USA). Sections from throughout the entire striatum were analyzed. Data are expressed as the ratio of evaluated DARPP-32 optical density (lesioned versus non-lesioned side). The optical density represents the average gray value within the section, corresponding to the sum of the gray values of all the pixels in the selection divided by the number of pixels. The corpus callosum and the anterior commissure were used to delineate the striatal area. Ventricular and striatal volumes were also determined on DARPP-32-stained sections throughout the entire striatum by use of the NIH-Image analysis program and are expressed as a percentage of the non-lesioned side. The number of ChAT- and NADPH-d-stained neurons were counted on between 9 and 12 sections per animal (200 μm between each section) throughout the entire striatum and are expressed as the percentage of neurons on the non-lesioned side.

Data Analysis

Data are expressed as mean±SEM and evaluated for analysis of variance (ANOVA) followed by a Scheffe's PLSD post-hoc test (JMP 3.0, SAS Institute Inc., USA). The significance level was set at $p<0.05$.

Example 1

Expression of IL-6 and IL-6R/IL-6 Chimera In Vitro

To compare the expression of a control gene (lacZ), IL-6 or IL-6R/IL-6 chimera, respectively, in a conventional transient transfection system versus a lentiviral expression system, the human embryonic kidney cell line 293T was either transfected with the plasmids SIN-W-PGK-nls-lacZ, SIN-W-PGK-IL-6 or SIN-W-PGK-IL-6R/IL-6 chimera plasmid or with lentiviral vectors containing either lacZ or IL-6 or IL-6R/IL-6 chimera.

At day 4, IL-6 and IL-6R/IL-6 chimera were measured in the cell supernatants by ELISA.

Figure 2:
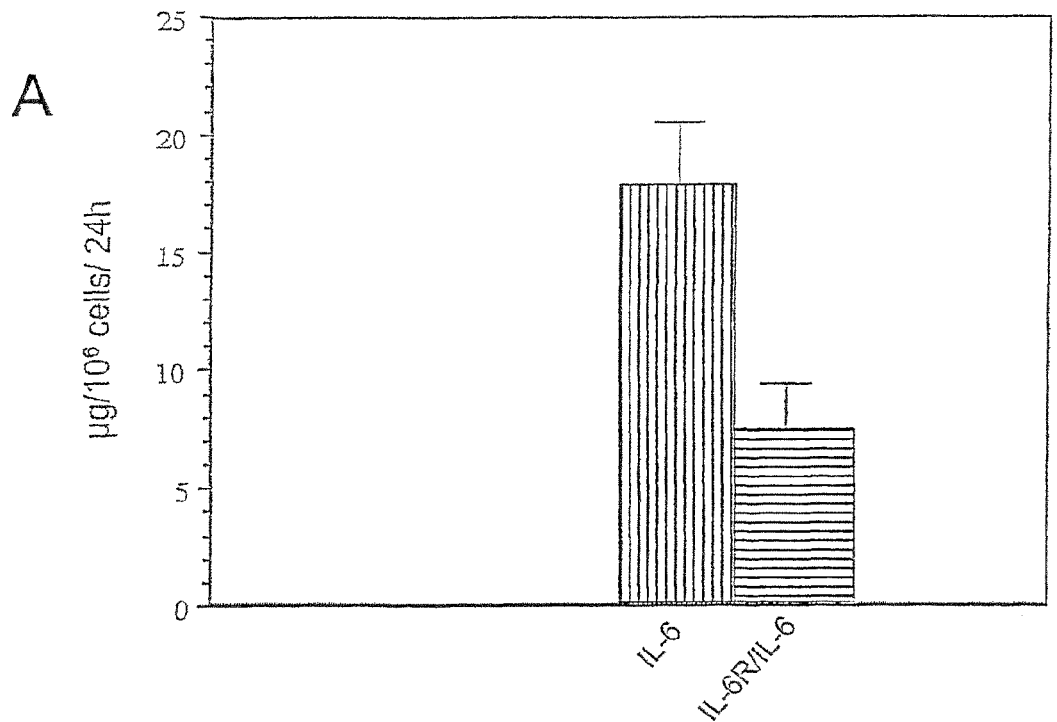
FIG. 2 shows the expression rate of lacZ (control). IL-6 and IL-6R/IL-6 chimera in the supernatants of 293 cells either transfected with an expression plasmid (FIG. 2 A) or infected with a lentivirus expression vector (FIG. 2 B) comprising the coding sequences of IL-6 (light gray) or IL-6R/IL-6 (dark gray), respectively.
Figure 2:
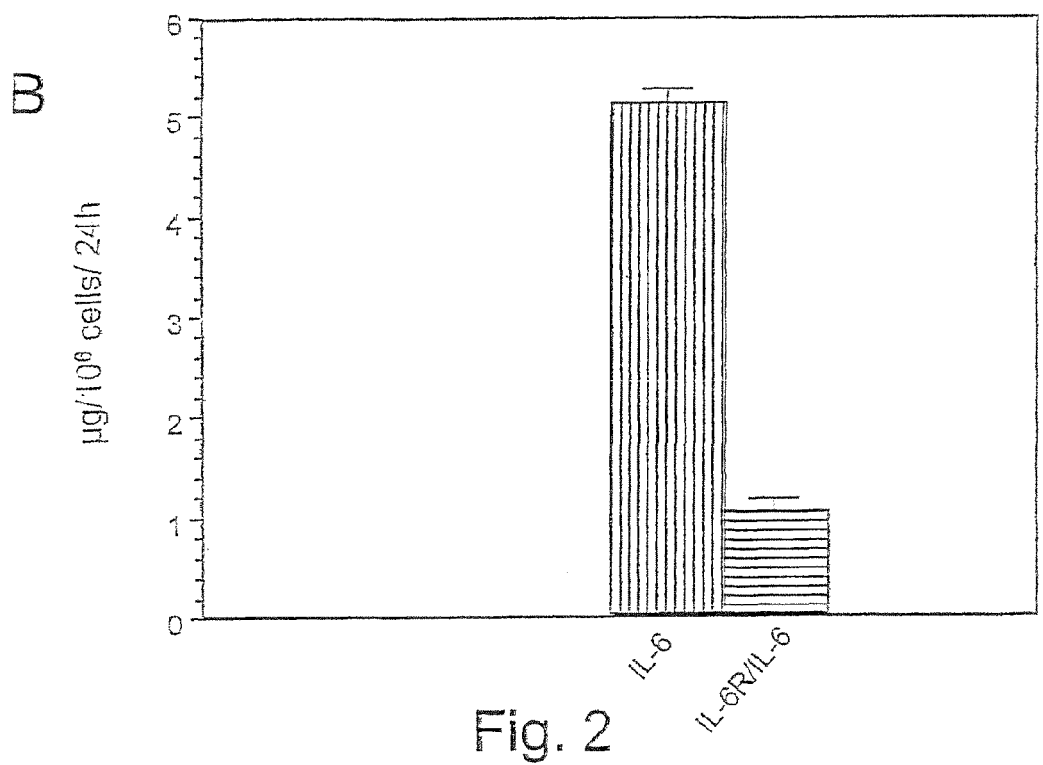

The results are shown in FIG. 2. IL-6 and IL-6R/IL-6 chimera can be expressed by tansfection (FIG. 2 A) and infection (FIG. 2 B). Transfection with an expression plasmid resulted in an expression rate about three times higher than infection with a lentiviral vector. IL-6 was expressed at a higher rate both by transfection and by infection, although the chimera was also expressed in high expression rates of about 7 $\mu g/10^6$ cells/24 hours by transfection and about 1 $\mu g/10^6$ cells/24 hours by infection.

These results show that both gene transfer procedures presented above are suitable for expression of the IL-6R/IL-6 chimera. Both recombinant cells and lentiviral vectors may therefore be used for delivery of the protein into the human body, especially into the brain, to exert its effect in treatment and/or prevention of HD.

Example 2

Lentiviral Vectors Expressing the IL-6 and IL-6R/IL-6

The in vivo production of IL-6 (n=5) and IL-6R/IL-6 (n=5) was measured on Wistar rats injected with 2 μl of the corresponding lentiviral vectors. Three weeks later, the animals were sacrificed and a 2 mm long punch covering the injection site was excised. The tissue was homogenized and analyzed by ELISA assay for IL-6 and IL-6R/IL-6. In the injected hemispheres, 11.9±7 ng IL-6 and 2.4±0.9 ng IL-6R/IL-6 were detected, whereas in the non-injected hemispheres values were below the background level. Immunohistochemical analysis of striatal sections indicated that both proteins, IL-6 as well as IL-6R/IL-6 chimera are expressed in a large area of the striatum (not shown). In agreement with previous reports, the number of GFAP-positive astrocytes increased in the animals injected with IL-6 and IL-6R/IL-6 compared to the LacZ and PBS groups (not shown).

Example 3

IL-6R/IL-6 Chimera Reduces the Extent of Apomorphine-Induced Rotation in Mice

QA is an excitotoxin inducing a characteristic lesion of neurons together with substantial atrophy of the striatum. Intrastriatal injection of QA mimics the pattern of selective neuronal vulnerability seen in HD. QA lesions further result in motor and cognitive deficits that are among the major symptoms seen HD. Therefore, intrastriatal injections of QA have become a useful model of HD and can serve to evaluate novel therapeutic strategies aimed at preventing, attenuating or reversing neuroanantomical and behavioral changes associated with HD.

Here, this model has been used to assess the ability of IL-6 and IL-6R/IL-6 chimera to ameliorate the detrimental effects resembling Huntington's disease.

Figure 3:
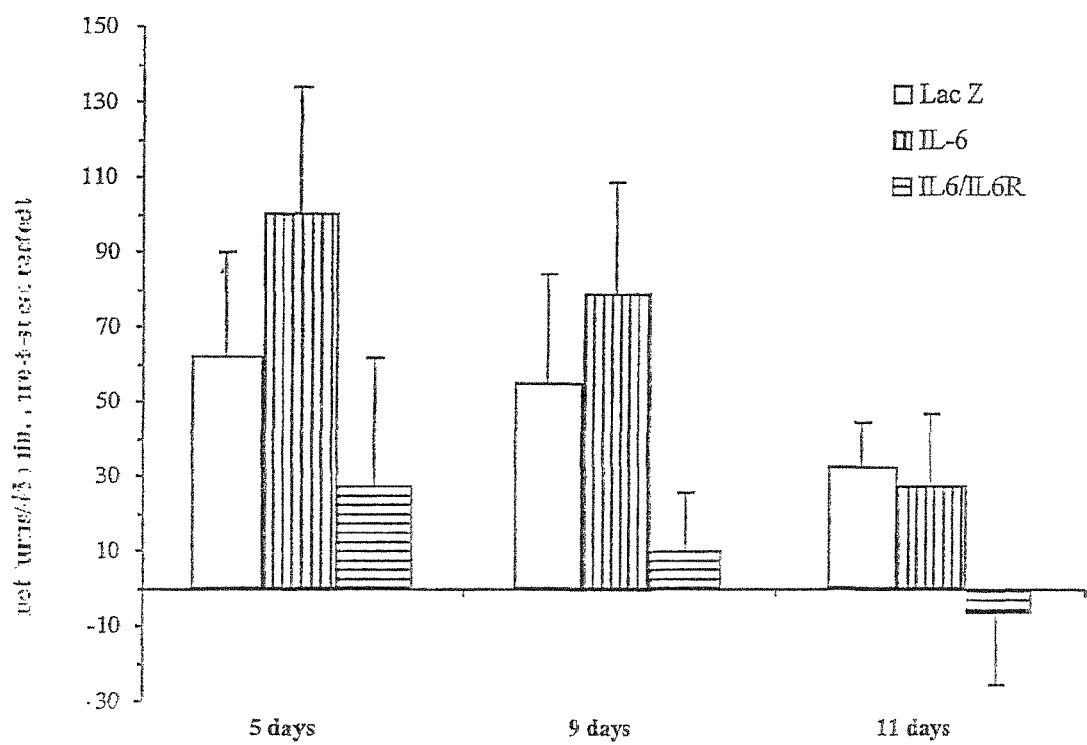
FIG. 3 shows the effect of LacZ (cotrol), IL-6 (vertical lines) and IL-6R/IL-6 chimera (horizontal lines) on apomorphine-induced rotational asymmetry 5, 9 and 11 days after the administration of QA. Positive values correspond to turns ipsilateral to the lesion. Values are expressed as mean±SEM.

To evaluate the neuroprotective effect of both proteins, 2 μl lentiviral vectors expressing the human IL-6 (n=6), the IL-6R/IL-6 chimera (n=6) and the LacZ reporter gene (n=6) were stereotaxically injected into the right striatum of adult rats. Three weeks later, the animals were lesioned by the intrastriatal injection of 180 nmol QA. The left hemisphere was untreated and served as an internal control. The apomorphine-induced rotational asymmetry was used to assess the striatal damage 5, 9 and 11 days after QA administration (Borlongan et al., 1995; Nakao & Brundin, 1997). While IL-6- and LacZ-treated animals showed atypical rotational behavior, a reduction of the asymmetry was observed in the IL-6R/IL-6 group (FIG. 3).

Whilst the presence of IL-6 increases the number of turns, thus aggravating the symptoms of disease, the presence of IL-6R/IL-6 chimera significantly reduces the number of turns shown by the animals. This protective effect of IL-6R/IL-6 chimera is already present 5 days post QA lesion, but is even more pronounced 9 and in particular 11 days post-lesion.

Example 4

Protection from QA-Induced Damage

In order to study whether the highly significant beneficial effect of IL-6R/IL-6 chimera shown in the behavioral study above correlates with a neuroprotective effect in the striatum, histological studies were carried out.

Figure 4:
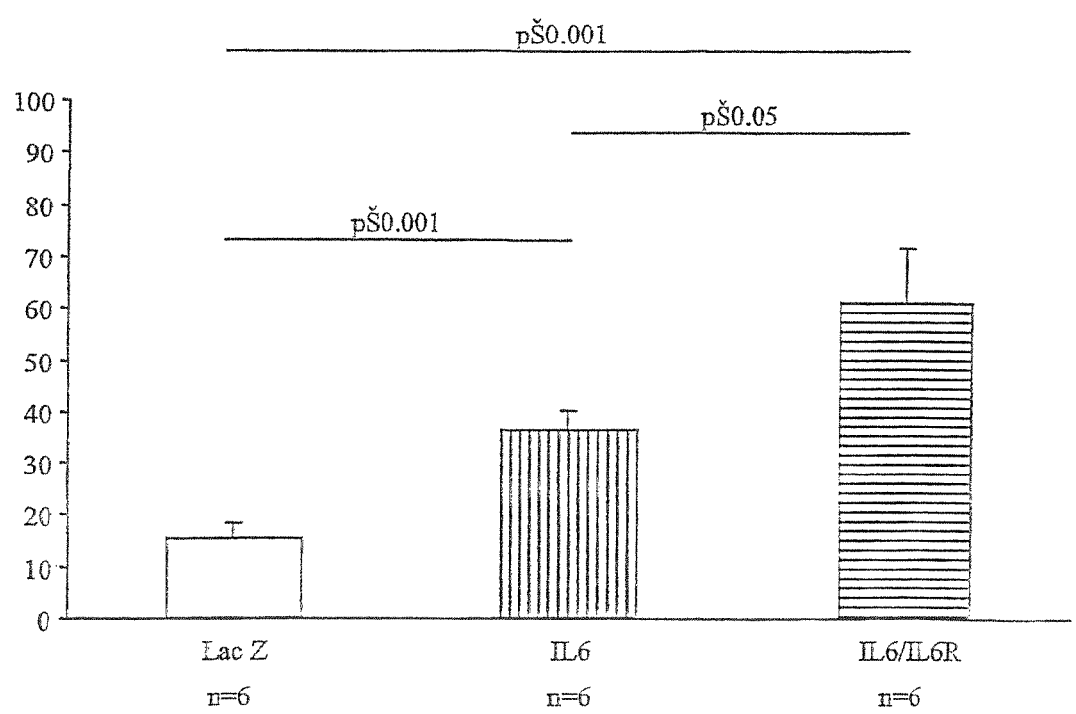
FIG. 4 shows quantification of the extent of the lesions based on the measurement of the optical density on DARPP-32-immunostained striatal sections from animals treated with lacZ (control), IL-6 (vertical lines) or IL-6R/IL-6 (horizontal lines). Values are expressed as mean±SEM.

No significant differences in the volume of the striatum or ventricle were observed between the ipsilateral and contralateral sides of the different groups. As expected, the QA lesion caused a shrinkage of the striatum (LacZ: 92.2%±2.1; IL-6: 91.7%±0.9; IL-6R/IL-6: 92.6%±1.7), and enlargement of the ventricle (LacZ: 186.5%±22.2; IL-6: 199.2%±22.1; IL-6R/IL-6: 180.9%±29.9) with conserved internal capsule fiber bundles. The optical density of DARPP-32 stained-sections a marker of GABAergic striatal neurons, was then used to determine the extent of the striatal lesion. In LacZ-injected animals QA induced a severe loss of DARPP-32 staining in the striatum in all animals. Photomicrographs depicting the stainings are not shown. Quantification of the extent of lesion based on the measurement of the optical density on DARPP-32 immunostained striatal lesions are shown in FIG. 4, expressed as mean±SEM. The loss of DARPP-32 immunoreactivity was attenuated in the IL-6-treated rats (LacZ: 84.3±2.9%; IL-6: 63.3±3.6%; p=0.001), but the neuroprotective effect was mainly limited to the medial striatal area close to the lateral ventricle. In contrast, most of the striatum was protected in the IL-6R/IL-6 group (38.6±10%; p=0.001).

Example 5

Protection of the Cholinergic and NADPH-d-Positive Interneurons

Figure 5:
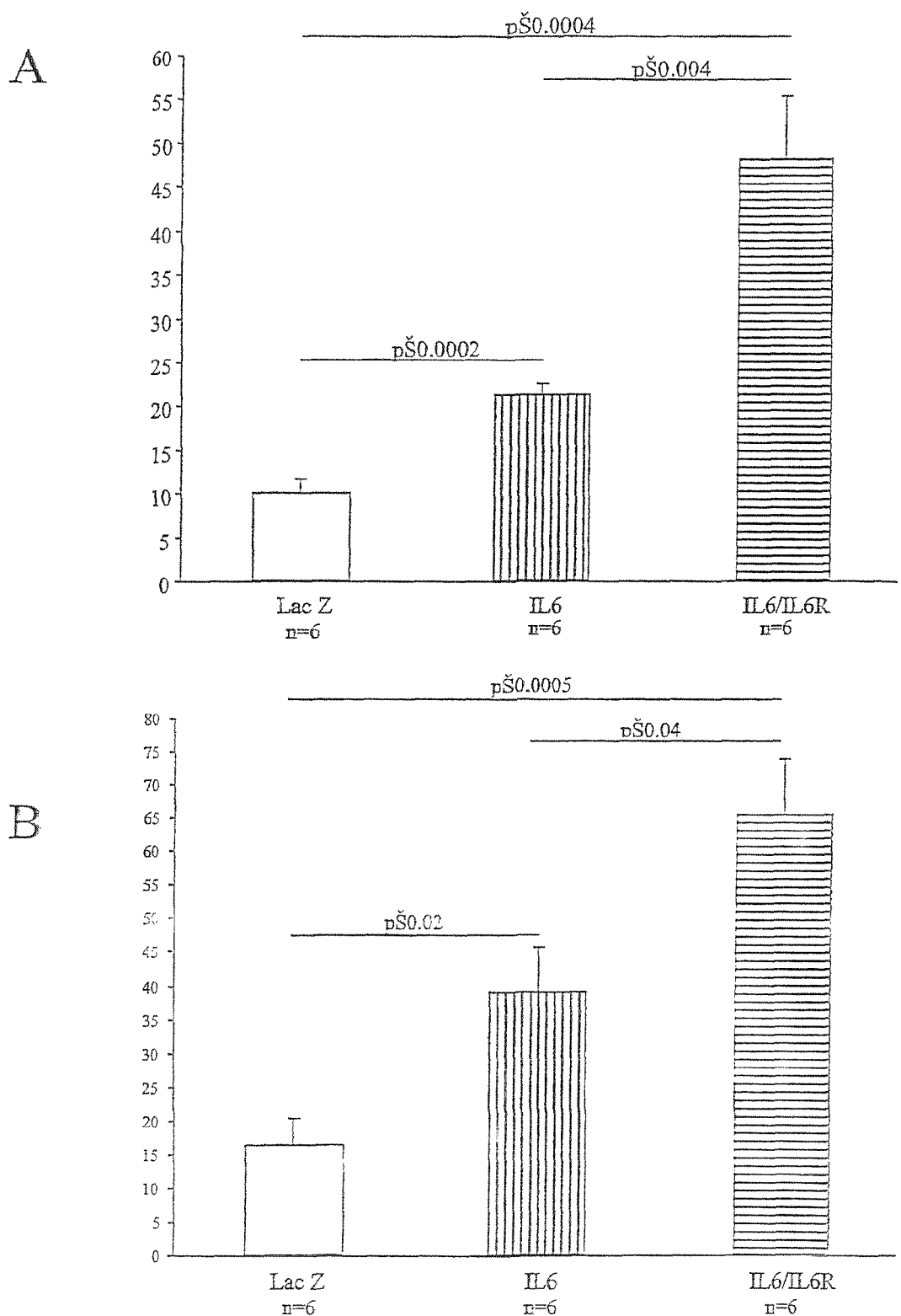
FIG. 5 shows the percentage of (A) NADPH-d-positive neurons, and (B) ChAT-positive neurons on the right (lesioned) side versus left (non-lesioned) side (n=6 per group) of animals treated with lacZ (control), IL-6 (vertical lines) or IL-6R/IL-6 (horizontal lines), respectively. Values are expressed as mean±SEM.

To further assess the effects of IL-6 and IL-6R/IL-6, two populations of interneurons were examined: the large aspiny cholinergic neurons (ChAT-positive) and the GABAergic interneurons, which express the nicotinamide adenine dinucleotide phosphate diaphorase (NADPH-d). In the LacZ control group, the percentage of ChAT and NADPH-d-positive cells in the QA-lesioned side was 16.6±3.7% compared to 10.2±1.5% in the non-lesioned side (FIGS. 5A and 5B). IL6 and IL-6R/IL-6 significantly prevented the degeneration of ChAT- and NADPH-d-immunoreactive neurons compared to the control group (IL-6=39.3±6.5%; IL-6R/IL-6=65.4±8.5%; p=0.02 and p=0.0005) (FIGS. 5A and 5B). In agreement with the results on DARPP-32 neurons, the magnitude of the effect was higher with the IL-6 chimera.

CONCLUSIONS

IL-6R/IL-6 chimera had a significant beneficial effect in a well-established experimental model of HD, demonstrating the therapeutic efficacy of the IL-6R/IL-6 chimera against the behavioral defects of Huntington's disease. In addition to that IL-6R/IL-6 exerted a neuroprotective effect in those regions of the brain affected by HD.

Taken together, the results shown above clearly demonstrate the efficacy of IL-6R/IL-6 chimera in the treatment and/or prevention of Huntington's disease. Thus, the present invention provides for a new possibility of treating and/or preventing HD, a so far incurable brain disorder.

REFERENCES

Anderson K D, Panayotatos N, Corcoran T L, Lindsay R M, Wiegand S J. Proc Natl Acad Sci USA. 1996 Jul. 9; 93(14): 7346-51
Altschul S F et al, J Mol Biol, 215, 403-410, 1990, Altschul S F et al, Nucleic Acids Res., 25:389-3402, 1997
Beal M F, Ferrante R J, Swartz K J, Kowall N W: J Neurosci. 1991 June; 11(6): 1649-59.
Bemelmans A P, Horellou P. Pradier L. Brunet I, Colin P. Mallet J Hum Gene Ther. 1999 Dec. 10; 10(18):2987-97.
Bensadoun J C, Deglon N. Tseng J L, Ridet J L, Zurn A D, Aebischer P Exp Neurol. 2000 July; 164(1):15-24
Borlongan, C. V., Randall, T. S., Cahill, D. W., and Sanberg, P. R. (1995). Asymmetrical motor behavior in rats with unilateral striatal excitotoxic lesions as revealed by the elevated body swing test. Brain Res., 676, 231-4.
Breighton, B and Hayden, M R: S Afr Med J. 1981 Feb. 21; 59(8): 250.
Chebath, J., Fischer, D., Kumar, A., Oh, J. W., Kollet, O., Lapidot, T., Fischer, M., Rose-John, S., Nagler, A., Slavin, S, and Revel, M. Eur. Cytokine Netw. 1997 8, 359-365.
Choi, D W: Neuron. 1988 October; 1(8):623-34. Review.
Deglon N. Tseng J L, Bensadoun J C, Zurn A D, Arsenijevic Y, Pereira de Almeida L. Zufferey R, Trono D, Aebischer P Hum Gene Ther. 2000 Jan. 1; 11(1):179-90.
Devereux J et al, Nucleic Acids Res, 12, 387-395, 1984.
Ellison D W, Kowall N R, Martin J B J Comp Neurol. 1987 Jun. 8; 260(2):233-45
Emerich D F, Cain C K, Greco C. Saydoff J A, Hu Z Y, Liu H. Lindner M D Cell Transplant. 1997 May-June; 6(3):249-66.
Emerich, D. F., Lindner, M. D., Winn, S. R., Chen, E.-Y., Frydel, B. R., and Kordower, J. H. (1996). J. Neurosci., 16, 5168-5181.
Emerich D F, Winn S R, Hantraye P M, Peschanski M, Chen E Y, Chu Y, McDermott P, Baetge E E, Kordower J H Nature. 1997 Mar. 27; 386(6623):395-9.
Emerich D F, Hammang J P, Baetge E E, Winn S R Exp Neurol. 1994 November; 130(1):141-50.
Fischer M. Goldschmitt J. Peschel C. Brakenhoff J P, Kallen K J, Wollmer A, Grotzinger J, Rose-John S. Nat Biotechnol. 1997 February; 15(2):142-5.
Gadient, R. A. and Otten, U. H. Prog. Neurobiol. 1997, 52, 379-390.
Greenamyre J T, Penney J B, Young A B, D'Amato C J, Hicks S P, Shoulson I: Science. 1985 Mar. 22; 227(4693):1496-9.
Haggiag S, Chebath J, Revel M FEBS Lett. 1999 Aug. 27; 457(2):200-4.
Halimi H, Eisenstein M. Oh J. Revel M and Chebath J. Eur. Cytokine Netw. 1995, 6: 135-143,
Hirano T, Matsuda T and Nakajima K: Stem cells 1994, 12:262-277.
Hirota H, Kiyama H, Kishimoto T, Taga T J Exp Med. 1996 Jun. 1; 183(6):2627-34.
Hottinger, A. F., Azzouz, M., Déglon, N., Aebischer, P., and Zurn, A. D. (2000). J. Neurosci., 20, 5587-93.
Katz, A., Chebath, J., Friedman, J., and Revel, M. (1998). Increased sensitivity of IL-6-deficient mice to carbon tetrachloride hepatotoxicity and protection with an IL-6 receptor-IL-6 chimera. *Cytokines Cell Mol. Ther.*, 4, 221-7.
Klimatcheva E. Rosenblatt J D, Planelles V Front Biosci. 1999 Jun. 1; 4:D481-96. Review.
Kordower J H, Bloch J. Ma S Y, Chu Y, Palfi S, Roitberg B Z, Emborg M, Hantraye P, Deglon N, Aebischer P Exp Neurol. 1999 November; 160(1):1-16
Kordower J H, Chen E Y, Winkler C, Fricker R. Charles V. Messing A, Mufson E J, Wong S C, Rosenstein J M, Bjorklund A, Emerich D F, Hammang J, Carpenter M K J Comp Neurol. 1997 Oct. 13; 387(1):96-113.
Kremer B, Goldberg P, Andrew S E, Theilmann J, Telenius H, Zeisler J, Squitieri F, Lin B, Bassett A, Almqvist E, et al: N Engl J Med. 1994 May 19; 330(20):1401-6.
Loeb J E, Cordier W S, Harris M E, Weitzman M D, Hope T J Hum Gene Ther. 1999 Sep. 20; 10(14):2295-305.
Lin B, Nasir J. Kalchman M A, McDonald H. Zeisler J. Goldberg Y P, Hayden M R Genomics. 1995 Feb. 10; 25(3):707-15.
Mendel, I., Katz, A., Kozak, N., Ben-Nun, A. and Revel, M. Eur. J. Immunol. 1998 28, 1727-1737.
Murakami M, Hibi M, Nakagawa N. Nakagawa T, Yasukawa K. Yamanishi K, Taga T, Kishimoto T Science. 1993 Jun. 18; 260(5115):1808-10.
Naldini L, Blomer U, Gage F H, Trono D, Verma I M Proc Natl Acad Sci USA. 1996 Oct. 15; 93(21):11382-8.

Novick, D., Shulman, L. M., Chen, L. and Revel, M. Cytokine 1992 4, 6-11.
Novick D, Shulman L M, Chen L and Revel M. Cytokine 1992, 4: 6-11,
Novick D. Engelmann H. Wallach D. Leitner O. Revel M. Rubinstein M. Journal of Chromatography 1990. 510:331-7.
Paonessa G, Graziani R, Deserio A, Savino R, Ciapponi L, Lahmm A, Salvati A L, Toniatti C and Ciliberto G. EMBO J. 1995:14:1942-1951.
Pearson W R, Methods in Enzymology, 183, 63-99, 1990
Pearson W R and Lipman D J, Proc Nat Acad Sci USA, 85, 2444-2448, 1988
Roberts R C, Ahn A, Swartz K J, Beal M F, DiFiglia M Exp Neurol. 1993 December; 124(2):274-82
Smith and Waterman J Mol Biol, 147,195-197, 1981, Advances in Applied Mathematics, 2, 482-489. 1981.
Strong T V, Tagle D A, Valdes J M, Elmer L W, Boehm K, Swaroop M, Kaatz K W, Collins F S, Albin R L Nat Genet. 1993 November; 5(3):259-65.
Taga, T., Hibin M., Hirata, Y., Yamasaki, K., Yasukawa, K., Matsuda, T., Hirano, T. and Kishimoto, T. Cell 1989 58, 573-581.
Toulmond, S., Vige, X., Fage, D., and Benavides, J. Neurosci Lett 1992, 144, 49-52.
Ward L D, Howlett G J, Discolo G. Yasukawa K. Hammacher A. Moritz R L and Simpson R J. High affinity interleukin-6 receptor is a hexameric complex consisting of two molecules each of interleukin-6, interleukin-6 receptor and gp130. J. Biol. Chem. 1994, 269: 23286-23289.
Yamada, M., and Hatanaka, H.: Brain Res 1994, 643, 173-80.
Zufferey R, Donello J E, Trona D, Hope T J J Virol. 1999 April; 73(4):2886-92.

The invention claimed is:

1. A method for attenuating or ameliorating the symptoms of Huntington's disease, comprising administering to a patient in need thereof
an effective amount of an IL-6R/IL-6 chimera, comprising:
   a) IL-6R having the sequence of residues 20-356 of SEQ ID NO:2;
   b) IL-6 having the sequence of residues 360-543 of SEQ ID NO:2; and
   c) optionally, a linker sequence between the sequences of a) and b), said linker sequence having a length of 1-18 residues;
   or a functional derivative or salt of said chimera, said chimera being glycosylated at one or more sites.

2. A method according to claim 1, wherein said IL-6R, IL-6 and optional linker sequence is fused to an immunoglobulin (Ig).

3. A method according to claim 1, wherein the functional derivative comprises at least one moiety attached to one or more functional groups which occur as one or more side chains on the amino acid residues.

4. A method according to claim 1, wherein said administering step comprises administering a cell expressing said chimera.

* * * * *